United States Patent
Blain et al.

(10) Patent No.: US 9,217,020 B2
(45) Date of Patent: Dec. 22, 2015

(54) CONSTRUCTS FOR ENHANCEMENT OF GENE EXPRESSION IN MUSCLE

(75) Inventors: Marilyne Blain, Lorraine (CA); Bernard Massie, Laval (CA); Renald Gilbert, Montreal (CA)

(73) Assignee: National Research Council of Canada, Ottawa (CA)

( * ) Notice: Subject to any disclaimer, the term of this patent is extended or adjusted under 35 U.S.C. 154(b) by 424 days.

(21) Appl. No.: 12/450,939

(22) PCT Filed: Apr. 14, 2008

(86) PCT No.: PCT/CA2008/000689
§ 371 (c)(1),
(2), (4) Date: Mar. 5, 2010

(87) PCT Pub. No.: WO2008/124934
PCT Pub. Date: Oct. 23, 2008

(65) Prior Publication Data
US 2012/0282695 A1 Nov. 8, 2012

Related U.S. Application Data

(60) Provisional application No. 60/907,777, filed on Apr. 17, 2007.

(51) Int. Cl.
*C12N 15/63* (2006.01)
*C12N 15/85* (2006.01)
*C12P 21/00* (2006.01)
*A61K 48/00* (2006.01)
*C07K 14/47* (2006.01)

(52) U.S. Cl.
CPC ............ *C07K 14/4716* (2013.01); *C12N 15/85* (2013.01); *A61K 48/00* (2013.01); *C12N 2799/027* (2013.01); *C12N 2830/008* (2013.01); *C12N 2830/85* (2013.01)

(58) Field of Classification Search
None
See application file for complete search history.

(56) References Cited

PUBLICATIONS

Thomas Gerster et al. Cell type specificity elements of the immunoglobulin heavy chain gene enhancer. The EMBO Journal, 1987. vol. 6, No. 5, pp. 1323-1330.*
Koji Goto et al. Functional Cooperation of Lens-specific and non-specific elements in the alpha1-Crystallin enhancer. Molecular and Cellular Biology, 1990. vol. 10, No. 3. pp. 958-964.*
Written Opinion and ISR on PCT-CA2008-000689 dated Jul. 29, 2008.
IPRP on PCT-CA2008-000689 dated Oct. 29, 2009.
Ratanamart, J. and Shaw, J. A. (2006). Plasmid-mediated muscle-targeted gene therapy for circulating therapeutic protein replacement: a tale of the tortoise and the hare? Curr. Gene Ther. 6: 93-110.
Goldspink, G. (2003). Skeletal muscle as an artificial endocrine tissue. Best. Pract. Res. Clin. Endocrinol. Metab 17: 211-222.
Lu, Q. L., Bou-Gharios, G., and Partridge, T. A. (2003). Non-viral gene delivery in skeletal muscle: a protein factory. Gene Ther. 10: 131-142.
Wang, L. and Herzog, R. W. (2005). AAV-mediated gene transfer for treatment of hemophilia. Curr. Gene Ther. 5: 349-360.
Sun, B. et al. (2005). Correction of glycogen storage disease type II by an adeno-associated virus vector containing a muscle-specific promoter. Mol. Ther. 11: 889-898.
Takahashi, H. et al. (2002). Long-term systemic therapy of Fabry disease in a knockout mouse by adeno-associated virus-mediated muscle-directed gene transfer. Proc. Natl. Acad. Sci. U. S. A 99: 13777-13782.
Tripathy, S. K. et al. (1996). Long-term expression of erythropoietin in the systemic circulation of mice after intramuscular injection of a plasmid DNA vector. Proc. Natl. Acad. Sci. U. S. A 93: 10876-10880.
Lu, Y. et al. (2006). Therapeutic level of functional human alpha 1 antitrypsin (hAAT) secreted from murine muscle transduced by adeno-associated virus (rAAV1) vector. J. Gene Med. 8: 730-735.
Athanasopoulos, T. et al. (2000). Intramuscular injection of a plasmid vector expressing human apolipoprotein E limits progression of xanthoma and aortic atheroma in apoE-deficient mice. Hum. Mol. Genet. 9: 2545-2551.
Harris, J. D. et al. (2002). Inhibition of atherosclerosis in apolipoprotein-E-deficient mice following muscle transduction with adeno-associated virus vectors encoding human apolipoprotein-E. Gene Ther. 9: 21-29.
Chamberlain, J. S. (2002). Gene therapy of muscular dystrophy. Hum. Mol. Genet. 11: 2355-2362.
Deconinck, N., Ragot, T., Marechal, G., Perricaudet, M., and Gillis, J. M. (1996). Functional protection of dystrophic mouse (mdx) muscles after adenovirus-mediated transfer of a dystrophin minlgene. Proc. Natl. Acad. Sci. U. S. A 93: 3570-3574.
Yang, Y., Haecker, S. E., Su, Q., and Wilson, J. M. (1996). Immunology of gene therapy with adenoviral vectors in mouse skeletal muscle. Hum. Mol. Genet. 5: 1703-1712.
Acsadi, G. et al. (1996). Dystrophin expression in muscles of mdx mice after adenovirus-mediated in vivo gene transfer. Hum. Gene Ther. 7: 129-140.
Ishii, A. et al. (1999). Effective adenovirus-mediated gene expression in adult murine skeletal muscle. Muscle Nerve 22: 592-599.
Pastore, L. et al. (1999). Use of a liver-specific promoter reduces immune response to the transgene in adenoviral vectors. Hum. Gene Ther. 10: 1773-1781.
Hauser, M. A. et al. (2000). Analysis of muscle creatine kinase regulatory elements in recombinant adenoviral vectors. Mol. Ther. 2: 16-25.
Hartigan-O'Connor, D., Kirk, C. J., Crawford, R., Mule, J. J., and Chamberlain, J. S. (2001). Immune evasion by muscle-specific gene expression in dystrophic muscle. Mol. Ther. 4: 525-533.

(Continued)

Primary Examiner — Celine Qian
(74) Attorney, Agent, or Firm — Sonia Patanaude

(57) ABSTRACT

Efficient and muscle-specific gene expression can be obtained with constructs containing two or more copies of USE and/or ΔUSE fused to the minimal promoter of the TnISlow gene. USE is a small (about 160-bp) upstream enhancer of the TnISlow gene that confers slow-twitch muscle fiber specificity. ΔUSE is generated from a 100-bp deletion at the 5' end of USE. ΔUSE confers expression in slow- and fast-twitch muscle fibers. The strength and relatively small size (less than 600-bp) of these constructs make them useful for gene therapy applications.

19 Claims, 9 Drawing Sheets

(56) References Cited

PUBLICATIONS

Cordier, L. et al. (2001). Muscle-specific promoters may be necessary for adeno-associated virus- mediated gene transfer in the treatment of muscular dystrophies. Hum. Gene Ther. 12: 205-215.

Hagstrom, J. N. et al. (2000). Improved muscle-derived expression of human coagulation factor IX from a skeletal actin/CMV hybrid enhancer/promoter. Blood 95: 2536-2542.

Corin, S. J., Levitt, L. K., O'Mahoney, J. V., Joya, J. E., Hardeman, E. C., and Wade, R. (1995). Delineation of a slow-twitch-myofiber-specific transcriptional element by using in vivo somatic gene transfer. Proc. Natl. Acad. Sci. U. S. A 92:6185-6189.

Nakayama, M., Stauffer, J., Cheng, J., Banerjee-Basu, S., Wawrousek, E., and Buonanno, A. (1996). Common core sequences are found in skeletal muscle slow- and fast-fiber-type-specific regulatory elements. Mol. Cell Biol. 16: 2408-2417.

Calvo, S., Vullhorst, D., Venepally, P., Cheng, J., Karavanova, I., and Buonanno, A. (2001). Molecular dissection of DNA sequences and factors involved in slow muscle-specific transcription. Mol. Cell Biol. 21: 8490-8503.

Yutzey, K. E., Kline, R. L., and Konieczny, S. F. (1989). An internal regulatory element controls troponin I gene expression. Mol. Cell Biol. 9: 1397-1405.

Hallauer, P. L. and Hastings, K. E. (2002). Tnlfast IRE enhancer: multistep developmental regulation during skeletal muscle fiber type differentiation. Dev. Dyn. 224: 422-431.

Larochelle, N. et al. (2002). The short MCK1350 promoter/enhancer allows for sufficient dystrophin expression in skeletal muscles of mdx mice. Biochem. Biophys. Res. Commun. 292: 626-631.

Hallauer, P. L., Bradshaw, H. L., and Hastings, K. E. (1993). Complex fiber-type-specific expression of fast skeletal muscle troponin I gene constructs in transgenic mice. Development 119: 691-701.

Yaffe, D. and Saxel, O. (1977). Serial passaging and differentiation of myogenic cells isolated from dystrophic mouse muscle. Nature 270: 725-727.

Gaillet, B. et al. (2007). High-Level Recombinant Protein Production in CHO Cells Using an Adenoviral Vector and the Cumate Gene-Switch. Biotechnol. Prog. 23: 200-209.

Massie, B. et al. (1998). New adenovirus vectors for protein production and gene transfer. Cytotechnology 28: 53-64.

Molnar, M. J. et al. (2004). Factors influencing the efficacy, longevity, and safety of electroporation-assisted plasmid-based gene transfer into mouse muscles. Mol. Ther. 10: 447-455.

Acsadi, G. et al. (1994). A differential efficiency of adenovirus-mediated in vivo gene transfer into skeletal muscle cells of different maturity. Hum. Mol. Genet. 3: 579-584.

Broussau, S. et al. (2008). Inducible Packaging Cells for Large-scale Production of Lentiviral Vectors in Serum-free Suspension Culture. Mol. Ther. 16: 500-507.

Miyoshi, H., Blomer, U., Takahashi, M., Gage, F. H., and Verma, I. M. (1998). Development of a self-inactivating lentivirus vector. J. Virol. 72: 8150-8157.

Vigna, E. et al. (2002). Robust and efficient regulation of transgene expression in vivo by improved tetracycline-dependent lentiviral vectors. Mol. Ther. 5: 252-261.

Gilbert, R., Broussau, S., and Massie, B. (2007). Protein production using lentiviral vectors. In Expression systems. (M. R. Dyson and Y. Durocher, Eds.), pp. 241-258, Scion.

Boshart, M., Weber, F., Jahn, G., Dorsch-Hasler, K., Fleckenstein, B., and Schaffner, W. (1985). A very strong enhancer Is located upstream of an immediate early gene of human cytomegalovirus. Cell 41: 521-530.

Niwa, H., Yamamura, K., and Miyazaki, J. (1991). Efficient selection for high-expression transfectants with a novel eukaryotic vector. Gene 108: 193-199.

Larochelle, N. et al. (1997). Efficient muscle-specific transgene expression after adenovirus-mediated gene transfer in mice using a 1.35 kb muscle creatine kinase promoter/enhancer. Gene Ther. 4: 465-472.

Brinster, R. L., Allen, J. M., Behringer, R. R., Gelinas, R. E., and Palmiter, R. D. (1988). Introns increase transcriptional efficiency in transgenic mice. Proc. Natl. Acad. Sci. U. S. A 85: 836-840.

Palmiter, R. D., Sandgren, E. P., Avarbock, M. R., Allen, D. D., and Brinster, R. L. (1991). Heterologous introns can enhance expression of transgenes in mice. Proc. Natl. Acad. Sci. U. S. A 88: 478-482.

Furger, A., O'Sullivan, J. M., Binnie, A., Lee, B. A., and Proudfoot, N. J. (2002). Promoter proximal splice sites enhance transcription. Genes Dev. 16: 2792-2799.

Okayama, H. and Berg, P. (1983). A cDNA cloning vector that permits expression of cDNA inserts in mammalian cells. Mol. Cell Biol. 3: 280-289.

Mir, L. M. et al. (1999). High-efficiency gene transfer into skeletal muscle mediated by electric pulses. Proc. Natl. Acad. Sci. U. S. A 96: 4262-4267.

Mathiesen, I. (1999). ElectropermeabilizatIon of skeletal muscle enhances gene transfer in vivo. Gene Ther. 6: 508-514.

Aihara, H. and Miyazaki, J. (1998). Gene transfer into muscle by electroporation in vivo. Nat. Biotechnol. 16: 867-870.

Vigna, E. and Naldini, L. (2000). Lentiviral vectors: excellent tools for experimental gene transfer and promising candidates for gene therapy. J. Gene Med. 2: 308-316.

Lever, A. M., Strappe, P. M., and Zhao, J. (2004). Lentiviral vectors. J. Biomed. Sci. 11: 439-449.

Sinn, P. L., Sauter, S. L. and McCray, P. B., Jr. (2005). Gene therapy progress and prospects: development of improved lentiviral and retroviral vectors—design, biosafety, and production. Gene Ther. 12: 1089-1098.

Xu, Z. L., Mizuguchi, H., Ishii-Watabe, A., Uchida, E., Mayumi, T., and Hayakawa, T. (2001). Optimization of transcriptional regulatory elements for constructing plasmid vectors. Gene 272: 149-156.

Gilbert, R., Liu, A., Petrof, B., Nalbantoglu, J., and Karpati, G. (2002). Improved performance of a fully gutted adenovirus vector containing two full-length dystrophin cDNAs regulated by a strong promoter. Mol. Ther. 6: 501-509.

Li, X., Eastman, E. M., Schwartz, R. J., and Draghia-Akli, R. (1999). Synthetic muscle promoters: activities exceeding naturally occurring regulatory sequences. Nat. Biotechnol. 17: 241-245.

Li, S. et al. (1999). Increased level and duration of expression in muscle by co-expression of a transactivator using plasmid systems. Gene Ther. 6: 2005-2011.

Frauli, M., Ribault, S., Neuville, P., Auge, F., and Calenda, V. (2003). Adenoviral-mediated skeletal muscle transcriptional targeting using chimeric tissue-specific promoters. Med. Sci. Monit. 9: BR78-BR84.

Skarli, M., Kiri, A., Vrbova, G., Lee, C. A., and Goldspink, G. (1998). Myosin regulatory elements as vectors for gene transfer by intramuscular injection. Gene Ther. 5: 514-520.

Danko, I. et al. (1997). High expression of naked plasmid DNA in muscles of young rodents. Hum. Mol. Genet. 6: 1435-1443.

Kumar, R. et al. (1986). Activation of gene expression is adversely affected at high multiplicities of linked simian virus 40 enhancer. Proc. Natl. Acad. Sci. USA. 83: 3199-3203.

Keogh M-C, et al. Design of a muscle cell-specific expression vector utilising human vascular smooth muscle a-actin regulatory elements. Gene Therapy. (1999) 6, 616-628.

Salva MZ, et al. Design of Tissue-specific Regulatory Cassettes for High-level rAAV-mediated Expression in Skeletal and Cardiac Muscle. Molecular Therapy. 15(2): 320-329, Feb. 2007.

Sax CM, et al. Species-Specific Lens Activation of the Thymidine Kinase Promoter by a Single Copy of the Mouse aA-CRYBP1 Site and Loss of Tissue Specificity by Multimerization. Molecular and Cellular Biology. vol. 10, No. 12, Dec. 1990, p. 6813-6816.

Barnhart KM, et al. Enhancer and Promoter Chimeras in Plasmids Designed for Intramuscular Injection: A Comparative In Vivo and In Vitro Study. Human Gene Therapy. (1998) 9: 2545-2553.

Blain M., et al. Strong Muscle-Specific Regulatory Cassettes Based on Multiple Copies of the Human Slow Troponin I Gene Upstream Enhancer. Human Gene Therapy. 21:127-134 (Jan. 2010).

Robert M-A, et al. Strength and muscle specificity of a compact promoter derived from the slow troponin I gene in the context of episomal (gutless adenovirus) and integrating (lentiviral) vectors. J Gene Med. (2012) DOI: 10.1002/jgm.2675.

Wang B., et al. Construction and analysis of compact muscle-specific promoters for AAV vectors. Gene Therapy. (2008) 15:1489-1499.

* cited by examiner

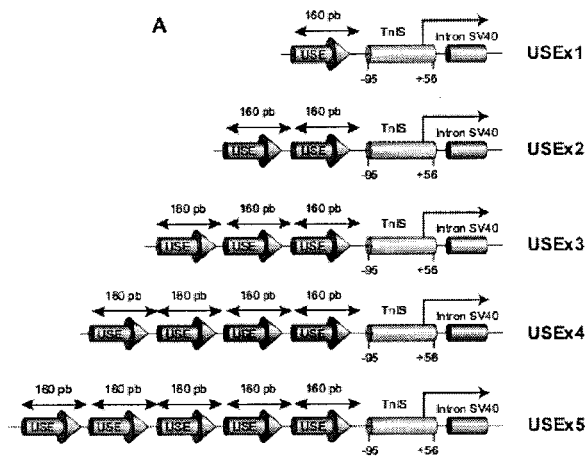

Fig. 1A

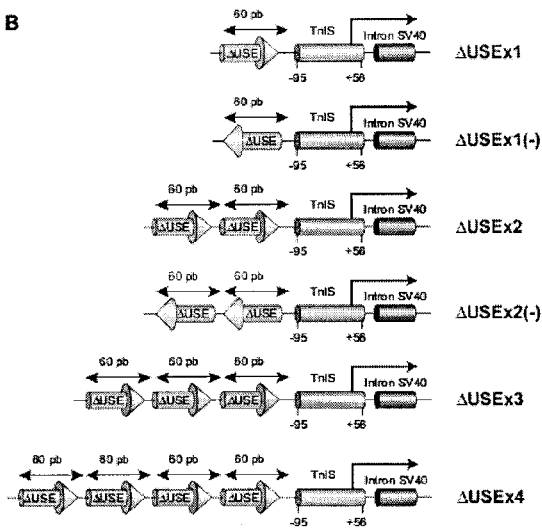

Fig. 1B

```
                                                              -1035
GAATTGGCGCGCCACTAGTCTCGAGGTACCGAGCTCTTACGCGTGCTAGCTCGAGATCTG

GGCCTCTGAGAGGGTCAGTGTCCTGCCCCAACCCATGAGATGACAGACTATAATAGCCAC

AGGATTAACATAGCAGGCATTGTCTTTCTCTGACTATAGGGTGGGTATTATGTGTTCATC
                                    -874        -95
AACCATCCTAAAAATACCCGGTAAACAGGTGCAGCCCCAGATCTGGGCAGCAGGAGGGGG

CAGTGGGTCTGTTCTATTTTTACCAGCCAGTTGCTGCTGGACACAGTTTTCATAGCCTCC

CCTCGGCTCTGCCCCTCACAGTCTGCAGTCTACGGCGAGGCACAGGCCAGCCCAGCTCCA
      +56
CGAGGACTGAACAAGAAGCTTGATATCGAATTGGTACCATCGAGGAACTGAAAAACCAGA

AAGTTAACTGGTAAGTTTAGTCTTTTGTCTTTATTTCAGGTCCCGGATCCGG
```

SEQ ID NO: 17

Fig. 1C

SEQUENCE LISTING

<160> NUMBER OF SEQ ID NOS: 17

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
cctagaagta aaggcgtatc cactgaggag cag         33

<210> SEQ ID NO 2
<211> LENGTH: 18
<212> TYPE: DNA
<213> ORGANISM: Artificial
<220> FEATURE:
<223> OTHER INFORMATION: Primer

<400> SEQUENCE: 2
cggtaaactg cccacttg         18

<210> SEQ ID NO 3

```
<211> LENGTH: 29
<212> TYPE: DNA
<213> ORGANISM: Artificial
<220> FEATURE:
<223> OTHER INFORMATION: Primer

<400> SEQUENCE: 3
gtactactag taccgagtct tacgcgtgc                                            29

<210> SEQ ID NO 4
<211> LENGTH: 37
<212> TYPE: DNA
<213> ORGANISM: Artificial
<220> FEATURE:
<223> OTHER INFORMATION: Primer

<400> SEQUENCE: 4
ggtacgtcta gataagcttc ccactgcccc ctcctgc                                   37

<210> SEQ ID NO 5
<211> LENGTH: 39
<212> TYPE: DNA
<213> ORGANISM: Artificial
<220> FEATURE:
<223> OTHER INFORMATION: Primer

<400> SEQUENCE: 5
gcggggagat ctggatatcg atatagggtg ggtattatg                                 39

<210> SEQ ID NO 6
<211> LENGTH: 37
<212> TYPE: DNA
<213> ORGANISM: Artificial
<220> FEATURE:
<223> OTHER INFORMATION: Primer

<400> SEQUENCE: 6
ggtacgtcta gataagcttc ccactgcccc ctcctgc                                   37

<210> SEQ ID NO 7
<211> LENGTH: 40
<212> TYPE: DNA
<213> ORGANISM: Artificial
<220> FEATURE:
<223> OTHER INFORMATION: Primer

<400> SEQUENCE: 7
gcggggacta gtggatatcg actatagggt gggtattatg                                40

<210> SEQ ID NO 8
<211> LENGTH: 37
<212> TYPE: DNA
<213> ORGANISM: Artificial
<220> FEATURE:
<223> OTHER INFORMATION: Primer

<400> SEQUENCE: 8
ggtacgtcta gataagcttc ccactgcccc ctcctgc                                   37

<210> SEQ ID NO 9
<211> LENGTH: 40
<212> TYPE: DNA
<213> ORGANISM: Artificial
<220> FEATURE:
<223> OTHER INFORMATION: Primer

<400> SEQUENCE: 9
```
ataggcgcgc cgtactagtg actatagggt gggtattatg                  40

<210> SEQ ID NO 10
<211> LENGTH: 36
<212> TYPE: DNA
<213> ORGANISM: Artificial
<220> FEATURE:
<223> OTHER INFORMATION: Primer

<400> SEQUENCE: 10
ataatacgcg ttaagcttcc cactgccccc tcctgc                      36

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
ctagtcgacg gctgcgtctg aggagaca                               28

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
ctactcgagg ccaagctccc tgaggaa                                27

<210> SEQ ID NO 13
<211> LENGTH: 19
<212> TYPE: DNA
<213> ORGANISM: Artificial
<220> FEATURE:
<223> OTHER INFORMATION: Primer

<400> SEQUENCE: 13
aacgacggcc agtgaattg                                         19

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
cagaccaatg gtgtgcaaga gc                                     22

<210> SEQ ID NO 15
<211> LENGTH: 41
<212> TYPE: DNA
<213> ORGANISM: Artificial
<220> FEATURE:
<223> OTHER INFORMATION: Primer

<400> SEQUENCE: 15
ccttaattaa gccggccagt gaattggcgc gccgtactag t                41

<210> SEQ ID NO 16
<211> LENGTH: 37
<212> TYPE: DNA

```
<213> ORGANISM: Artificial
<220> FEATURE:
<223> OTHER INFORMATION: Primer

<400> SEQUENCE: 16
aataccggtc ctccagttcc tcgatggtac caattcg                              37

<210> SEQ ID NO 17
<211> LENGTH: 474
<212> TYPE: DNA
<213> ORGANISM: Artificial
<220> FEATURE:
<223> OTHER INFORMATION: USEx1 construct

<400> SEQUENCE: 17
gaattggcgc gccactagtc tcgaggtacc gagctcttac gcgtgctagc tcgagatctg      60
ggcctctgag agggtcagtg tcctgcccca acccatgaga tgacagacta taatagccac     120
aggattaaca tagcaggcat tgtctttctc tgactatagg gtgggtatta tgtgttcatc     180
aaccatccta aaaatacccg gtaaacaggt gcagcccag atctgggcag caggaggggg      240
cagtgggtct gttctatttt taccagccag ttgctgctgg acacagtttt catagcctcc     300
cctcggctct gcccctcaca gtctgcagtc tacggcgagg cacaggccag cccagctcca    360
cgaggactga acaagaagct tgatatcgaa ttggtaccat cgaggaactg aaaaaccaga    420
aagttaactg gtaagtttag tcttttttgtc ttttatttca ggtcccggat ccgg         474
```

CONSTRUCTS FOR ENHANCEMENT OF GENE EXPRESSION IN MUSCLE

CROSS-REFERENCE TO RELATED APPLICATIONS

This application is a national entry of PCT/CA2008/000689 filed Apr. 14, 2008, which claims the benefit of United States Provisional Patent Application U.S. Ser. No. 60/907,777 filed Apr. 17, 2007, which is herein incorporated by reference in its entirety.

FIELD OF THE INVENTION

The present invention relates to regulatory elements for controlling gene transfer and/or expression, particularly in muscle, and to methods for expressing genes in muscle.

BACKGROUND OF THE INVENTION

The ability to achieve high-level and long-term recombinant protein expression after gene transfer in skeletal muscle is a crucial issue in the field of gene therapy. Because skeletal muscle is an important tissue that is readily accessible and that is highly vascularized, it could be used as a factory to produce proteins with therapeutic values (reviewed in [1-3]). Indeed, it has been demonstrated that functional therapeutic proteins can be synthesized by the skeletal muscle and secreted into the blood circulation in sufficient amount to mitigate the pathology associated with disorders such as hemophilia, Pompe disease, Fabry's disease, anaemia, emphysema, and familial hypercholesterolemia for example [4-10]. The ability to express recombinant proteins in skeletal muscle is also an important issue for the treatment of neuromuscular disorders such as Duchenne and limb girdle muscular dystrophy. These disorders are caused by mutations of a gene that produces an essential muscle protein. One potential treatment for such disorders is gene transfer, whose objective is to introduce into the muscle a normal and functional copy of the gene that is mutated (reviewed in [11, 12]).

Although high-level of recombinant protein production can be achieved after gene transfer in skeletal muscle using cis-acting DNA elements (promoter and enhancers) derived from viruses [13-16], these regulatory elements are not cell-specific. Besides the safety issues and potential toxicity associated with non-specific protein expression in different tissues of the body, recombinant proteins that are controlled by enhancer/promoter elements derived from viruses are more immunogenic than those produced in a tissue-specific manner, because they are more likely to be expressed in specialized antigen presenting cells [5, 17-20]. As a result, the use of tissue-specific enhancer/promoters, such as those that are active only in skeletal muscle, can prolong and stabilize the production of recombinant protein in vivo. The major drawback of using tissue specific regulatory elements is their strength, which is usually weaker than those derived from viruses [16, 18, 19, 21]. This implies that additional copies of the transgene (or vector carrying it) are necessary to produce sufficient proteins to achieve therapeutic value if a weaker combination of enhancer/promoter is used. In addition to increasing its cost, this may reduce the safety and increase the toxicity of the therapy. An ideal enhancer/promoter combination for gene transfer to skeletal muscle should be strong and muscle-specific. Because the transport capacity of some promising viral vectors is limited, the combination of enhancer/promoter elements carried by these vectors should be relatively small (less than 1-kb). Furthermore, because the skeletal muscle consists of a mixture of fast-twitch and slow-twitch muscle fibers, the enhancer/promoter elements should be active also in both types of fibers to maximize the protein production level.

Troponin I is an abundant component of the thin filament of myofibrils of striated muscle. In adult vertebrate skeletal muscles, two isoforms, the slow (TnISlow) and the fast (TnIFast) isoforms, that are expressed in fast-twitch and slow-twitch muscle fibers and that are encoded by two different genes, exist. The regulatory elements controlling the expression of TnISlow and TnIFast are relatively well characterized. In the case of TnISlow, a small upstream enhancer of about 160-bp (USE) also referred to as SURE, confers slow fiber type specificity [22, 23]. If a fragment of 100-bp is deleted at the 5' end of USE, the resulting enhancer (ΔUSE) remains muscle specific, but is now able to confer expression in slow-twitch as well as fast-twitch muscle fibers [24]. Specific expression of the TnIFast in fast-twitch muscle fibers is controlled by a 150-bp enhancer known as IRE or FIRE located within the first intron of that gene [23, 25, 26].

Thus, there is a need in the art for strong, muscle-specific regulatory elements for controlling gene transfer and/or expression in muscles.

SUMMARY OF THE INVENTION

It has now been found that surprisingly strong constructs for controlling gene expression can be obtained by multimerization of slow troponin I gene enhancers. The constructs are advantageously strong and small in size, making them useful for gene therapy. The constructs are advantageously muscle cell-specific.

There is provided a construct comprising two or more enhancers from a slow troponin I gene fused in line and operably linked to a muscle cell specific promoter.

There is provided a method of expressing a nucleotide sequence of interest in a muscle cell comprising transfecting into the muscle cell a construct comprising two or more enhancers from a slow troponin I gene fused in line and operably linked to a muscle cell specific promoter, the construct operably linked to the nucleotide sequence of interest.

There is provided a use of a construct of the present invention for expressing a nucleotide sequence of interest in a muscle cell.

Constructs of the present invention contain two or more enhancers or three or more enhancers. In one aspect, there may be up to five enhancers. In one embodiment, the construct can comprise three enhancers, in another embodiment the construct can comprise four enhancers, and in another embodiment the construct can comprise five enhancers.

The enhancers may be, for example, upstream enhancers of the slow troponin I (TnISlow) gene (e.g. USE and/or ΔUSE). Each enhancer may comprise a nucleotide sequence corresponding in nucleotide identity to a nucleotide sequence taken from a region of the TnISlow gene from −1045 to −870 relative to the transcription start site of the TnISlow gene. The TnISlow gene may be that of any vertebrate species, for example, humans and rats. In one embodiment, USE has a nucleotide sequence corresponding to nucleotides −1035 to −874 of the human TnISlow gene relative to the transcription start site of the gene, while ΔUSE has a nucleotide sequence corresponding to nucleotides −940 to −874 of the human TnISlow gene relative to the transcription start site of the gene. The line of enhancers may comprise only one type of enhancer or a combination of types of enhancers. The enhancers may be in natural (+), reverse (−), or a combination of natural and reverse orientations. In one embodiment, the enhancers are all in the natural orientation. The enhancers are generally upstream of the promoter.

The promoter is a muscle cell-specific promoter, for example a minimal TnISlow promoter, a minimal TnIFast promoter or a muscle creatine kinase promoter. In one embodiment, the promoter is a minimal TnISlow promoter. The promoter may comprise one or more exons. For example, the minimal TnISlow promoter may comprise nucleotides from −95 to +56 of the human TnISlow gene relative the transcription start site, which includes the first exon. The promoter is generally downstream of the enhancers. The promoter may be fused directly to the line of enhancers.

One or more introns may be included in the construct to improve level and stability of gene expression in vivo. Any suitable intron may be used. Modification to the introns may be required to prevent unwanted effects, for example the formation of fusion proteins. Some examples of suitable introns include synthetic introns (e.g. IVS intron of Clontech), introns derived from vertebrate genes (e.g. rat insulin II gene, human β-globin gene, rat growth hormone gene, human β-actin gene) or introns derived from virus genes (e.g. SV40 small T antigen gene, CMV immediate-early 1 gene). Introns are generally downstream of the promoter.

The construct may further comprise a nucleotide sequence of interest. The nucleotide sequence of interest is operably linked to the promoter downstream of the promoter. The nucleotide sequence of interest may be any gene or other nucleotide sequence for which expression is desired. For example, the nucleotide sequence of interest may code for a protein, for example a protein that mitigates pathology associated with a disorder, e.g. hemophilia, Pompe disease, Fabry's disease, anaemia, emphysema, and familial hypercholesterolemia. Nucleotide sequences that express proteins important in the functioning of muscles, e.g. skeletal muscles, are of particular interest, especially for treating a neuromuscular disorder, for example Duchenne and limb girdle muscular dystrophy.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1 depicts structures of constructs derived from human TnISlow gene: A) constructs made with upstream slow enhancer (USE), B) constructs made with truncated USE (ΔUSE), and C) nucleotide sequence of USE×1 construct (SEQ ID NO: 17).

DESCRIPTION OF PREFERRED EMBODIMENTS

Figure 2:
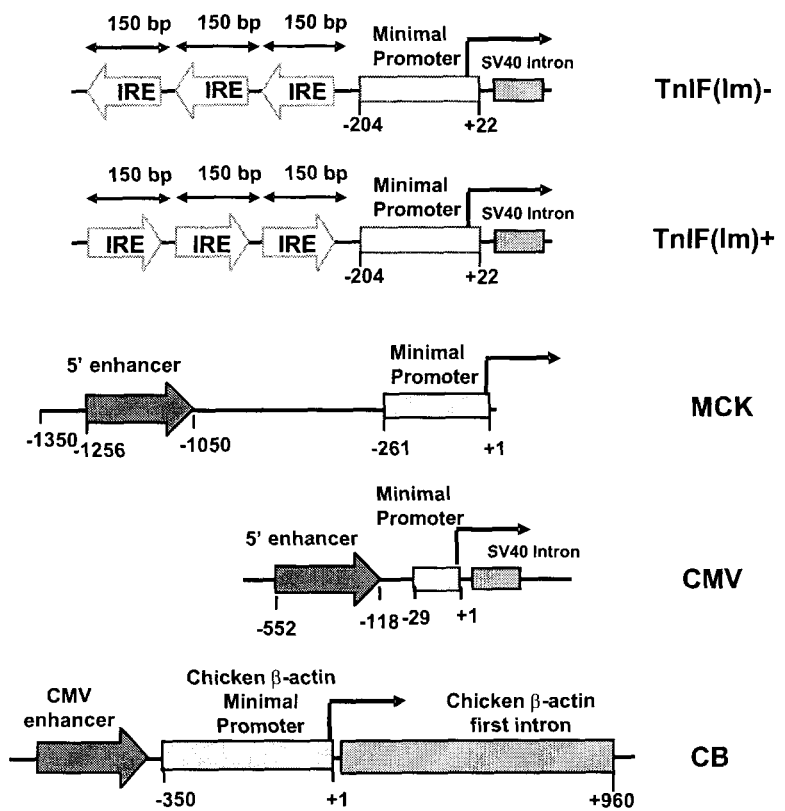
FIG. 2 depicts muscle-specific and viral derived constructs used for comparison.

Materials and Methods:
Preparation of Enhancer/Promoter Constructs

Plasmids were prepared using standard methods of molecular biology and they were purified by using the Plasmid Maxi Kit (Qiagen Inc, Mississauga, On, Canada) according to the manufacture's recommendations. The nucleotide sequences of the various constructs made were confirmed by DNA sequencing. Plasmid (pCMVβ), which encodes the enzyme β-galactosidase (β-gal) regulated by the CMV early enhancer/promoter, was purchased from Clontech Laboratories (Palo Alto, Calif.). Plasmid pCMVImβ was constructed by replacing the ATGTT sequence within the SV40 intron of pCMVβ with ATATC. The intron was amplified by PCR using primers 5'-CCTAGAAGTAAAGGCGTATCCACTGAG-GAGCAG-3' (SEQ ID NO: 1) and 5'-CGGTAAACTGC-CCACTTG-3' (SEQ ID NO: 2). The PCR product was digested with XhoI and inserted into the StuI and XhoI sites of pCMVβ. A plasmid expressing β-gal controlled by the MCK enhancer/promoter (pMCKβ) was constructed by removing the MCK enhancer/promoter of pAdMCKBecker [27] by digestion with KpnI and BlgII. The CMV enhancer/promoter and intron of pCMVβ were replaced with MCK by digesting pCMVβ with EcoRI and SmaI and by ligating the two fragments together. Before ligation, BlgII linkers were added to the ends of both fragments.

A plasmid (pTnIS(Im)β) expressing β-gal regulated by one copy of USE (from −1035 to −874) linked to the human minimal TnISlow promoter and first exon (from −95 to +56) was constructed by removing the USE/promoter fragment of TnI$_S$USE-95X1nucZ [22] by EcoR1/KpnI digestion. The EcoRI end was changed to KpnI using a linker and the insert was cloned into the unique KpnI site of plmβ. The latter plasmid was generated by replacing the CMV enhancer/promoter of pCMVImβ (EcoRI/Xho1 digestion) with a linker encoding four restriction sites (AscI, SpeI, KpnI, Xho1).

Constructs containing two to five copies of USE were prepared by inserting additional USE enhancers into the SpeI site of pTnIS(Im)β. The USE was amplified by PCR using primers 5'-GTACTACTAGTACCGAGTCTTACGCGTGC-3' (SEQ ID NO: 3) and 5'-GGTACGTCTAGATAAGCTTC-CCACTGCCCCCTCCTGC-3' (SEQ ID NO: 4) and pTnIS (Im)β as template. The PCR product was digested with XbaI and SpeI before ligation. Constructs (pTnIS(Im)β-ΔUSE), containing one copy of ΔUSE (from −940 to −874) in the natural (+) or reverse (−) orientation linked to the TnISlow minimal promoter and first exon were made by amplifying ΔUSE using primers 5'-GCGGGGAGATCTGGATATC-GATATAGGGTGGGTATTATG-3' (SEQ ID NO: 5) and 5'-GGTACGTCTAGATAAGCTTCCCACTGC-CCCCTCCTGC-3' (SEQ ID NO: 6) and pTnIS(Im)β as template. The PCR product was digested with BglI and inserted into pTnIS(Im)β previously digested with BlgII to remove the USE enhancer. Constructs containing two to four copies of ΔUSE in the natural (+) orientation and two copies ΔUSE in the reverse (−) orientation were generated by amplifying by PCR the ΔUSE enhancer using pTnIS(Im)β as template and the following primer pairs:

```
                                       (SEQ ID NO: 7)
5'-GCGGGGACTAGTGGATATCGACTATAGGGTGGGTATTATG-3'
and
                                       (SEQ ID NO: 8)
5'-GGTACGTCTAGATAAGCTTCCCACTGCCCCCTCCTGC-3'
or
                                       (SEQ ID NO: 9)
5'-ATAGGCGCGCCGTACTAGTGACTATAGGGTGGGTATTATG-3'
and
                                       (SEQ ID NO: 10)
5'-ATAATACGCGTTAAGCTTCCCACTGCCCCCTCCTGC-3'.
```

The PCR products were digested by SpeI and XbaI and inserted into the unique SpeI site of pTnIS(Im)β-ΔUSE(+) or pTnIS(Im)β-ΔUSE(−).

A plasmid (pTnIF(Im)β−) containing three copies of the first intron regulatory element (IRE) of the quail TnIFast gene in the reverse orientation (−) fused upstream to the minimal promoter of that gene and expressing β-gal was generated. The IRE (position +658 to +804) was amplified by PCR using construct TnIlacZ1 [28] as template and primers: 5'-CTAGTCGACGGCTGCGTCTGAGGAGACA-3' (SEQ ID NO: 11) and 5'-CTACTCGAGGCCAAGCTCCCTGAG-GAA-3' (SEQ ID NO: 12). The PCR product was digested with XhoI and SalI, ligated with itself, digested with XhoI and SalI and cloned into the SalI site of pBluescript II SK+ (Stratagene, LaJolla, Calif.). The fragment containing the minimal promoter (position −204 to +22) of the TnIFast gene [28] was subcloned from the plasmid gCTnIF(−198:+22)Z downstream of the 3×IREs into the HindIII and EcoRI sites. The fragment containing the 3×IRE and the minimal promoter was then removed by digestion with XhoI and KpnI and inserted into the XhoI and KpnI sites of p(Im)β. A plasmid encoding three copies of IRE and the natural orientation (+) linked to the minimal TnIFast promoter (pTnIF(Im)β+) was constructed by isolating the three IREs of pTnIF(Im)β− by PCR using primers 5'-AACGACGGCCAGTGAATTG-3' (SEQ ID NO: 13) and 5'-CAGACCAATGGTGTGCAA-GAG-C-3' (SEQ ID NO: 14). The PCR product was digested with XhoI and SalI and inserted into p(Im)β previously digested with XhoI. The TnIFast minimal promoter was isolated from pTnIF(Im)β− by digestion with SalI and KpnI and inserted downstream of the three IREs at the XhoI and KpnI sites of the previous plasmid.

Cells Culture and Transfection

Unless stated otherwise, the culture media and sera were purchased from Wisent Inc and Hyclone. 293A, A-549, HeLa cells were grown in Dulbecco's modified Eagle's medium (DMEM) supplemented with 5% fetal bovine serum (FBS) and 2 mM L-glutamine. C2C12 myoblasts [29] were grown in DMEM supplemented with 10% FBS and 2 mM L-glutamine. All cells were grown under standard conditions in a humidified incubator at 37° C. and 5% $CO_2$. For transfection, the cells were plated in 24-well dishes at a density of $4 \times 10^4$ (C2C12), $7 \times 10^4$ (HeLa and A-549) or $8 \times 10^4$ cells (293A) cells/well. The next day, they were transfected with 1 μg of plasmid using Lypofectamine 2000 (Invitrogen, Carlsbad Calif.) according to manufacturer's recommendation. The plasmids were spiked with an equal amount of a second plasmid (pAdCMV5SEAP) expressing the secreted alkaline phosphatase (SEAP) regulated the CMV enhancer/promoter. This plasmid was constructed by replacing the CR5 promoter of pAdSEAP [30] with CMV5 [31]. The formation of myotubes was induced by replacing the medium with DMEM supplemented with 2% horse serum (Sigma, ST-Louis, Mo.) and 2 mM L-glutamine, 24 h after transfection. The cells were lysed 48 h (293A, A-549, Hela, C2C12 myoblasts) or 11 days (C2C12 myotubes) after the start of the transfection. The β-gal activity was determined by luminometry using the β-gal chemiluminescent Reporter Gene Assay (Roche Molecular Biochemicals, Mannheim, Germany) according to the manufacturer's recommendations. The SEAP activity in the culture medium was determined at the time of cell lysis as described previously [30]. The transfection efficiency was normalized to the SEAP activity. Some cells were also fixed with 0.5% glutaraldehyde in PBS for 3 min at room temperature. The β-gal expression was then visualized by incubation with X-gal (5-bromo-4-chloro-3-indolyl-β-D-galactoside) using standard procedures.

Plasmid Electrotransfer in Mouse Muscle

The animal experiments were performed according to McGill University guidelines for animal care. Plasmid DNA for in vivo study was purified using the Endofree plasmid Maxi Kit (Qiagen Inc, Mississauga, On) according to the manufacturer's recommendation. Adult (5- to 6-week-old) normal (CD1, Charles River Laboratories) mice were used. The tibialis anterior muscle (TA) was injected with 30 μl of 0.4 U/μl hyaluronidase (Sigma-Aldrich, St. Louis, Mo., USA) diluted in saline. Two h later, 30 μl of plasmid (see below) diluted in PBS was injected into the TA followed by the application of an electric courant (electrotransfer) of eight pulses of 175 Volt/$cm^2$ (duration: 20 ms; interval: 1 sec) using an electroporation system (ECM 830; Genetronix, Inc., from BTX) with paddle circular electrodes (7 mm in diameter) as described previously [32]. Two experiments were performed. In the first, for each of the four plasmids encoding β-gal (CMV, CB, USE×3, ΔUSE×3), 6 muscles were injected with 1 μg/μl of plasmid. In the second experiments, 8 muscles were injected with the same plasmids that were mixed with an equal amount of plasmid expressing luciferase regulated by the CMV promoter [33]. The mice were sacrificed 10 days later and the entire TA were removed and frozen in liquid nitrogen-cooled isopentane. 10-μm-section were prepared for β-gal histochemistry as described previously [33]. Cryostat sections were also re-suspended in lysis buffer and the β-gal activity was measured by luminometry using the β-gal chemiluminescent Reporter Gene Assay (Roche Molecular Biochemicals, Mannheim, Germany) using the manufacturer's recommendations. The total protein concentration of the muscle lysate was determined using the DC protein assay (Bio-Rad).

Construction of Lentiviral Vectors

The ΔUSE×3 promoter, without the intron, was isolated by PCR using pTnIS-ΔUSE×3 as template and 5'-CCTTAAT-TAAGCCGGCCAGTGAATTGGCGCGCCGTACTAGT-3' (SEQ ID NO: 15) and 5'-AATACCGGTCCTCCAGTTC-CTCGATGGTACCAATTCG-3' (SEQ ID NO: 16) as primers. After phosphorylation with T4 polynucleotide kinase (New England Biolabs), the PCR product was cloned into the SmaI site of pUC19. The nucleotide sequence of the PCR product was confirmed by the DNA sequencing services of Université Laval (Quebec, QC). The GFP gene was isolated from pCSII-CMV-GFPq [34] by digesting this plasmid with BamHI and it was inserted into the unique BamHI site of pTetO7-5-mcs (see below), thus generating pTetO7-GFP. The ΔUSE×3 promoter was removed from pUC19 by digestion with PacI and AgeI and inserted upstream of the GFP gene of pTetO7-GFP previously digested with PacI and AgeI. The resulting transfer vector, called pTetO7-5-mcs-ΔUSE×3-GFP, was amplified and purified using the DNA maxiprep purification kit (Qiagen, Valentia, Calif.) according to the manufacturer's recommendations. To construct pTetO7-5-msc, we first generated pTetO7-CSII-CMV-mcs by introducing the Tet07 promoter into the 3'LTR of pCSII-CMV-mcs [35]. The Tet07 promoter was removed from pLVR2-GFP [36] by digestion with BsmI and XhoI. The fragment containing the Tet07 promoter was ligated into pCSII-CMV-mcs previously digested with PmeI and BspEI. To perform the ligation, the XhoI end was replaced with a BsPE1 linker and the BsMI ends were blunted using T4 DNA polymerase. The CMV promoter of Tet07-CSII-CMV-msc was then removed by PCR and a unique PacI was inserted at the 5' end of the multiple cloning site, thus generating pTet07-5-msc.

Production of Lentiviral Vectors

LV expressing GFP regulated by CMV (LV-CMV-GFP) or by ΔUSE×3 (LV-ΔUSE×3-GFP) were produced as described previously [34, 37]. Briefly, the 293SF-PacLV cells [34] were transfected with pTetO7-ΔUSE×3-GFP or pTetO7-5-mcs-CMV-GFP [34] using a mixture of DNA and polyethylenimine, (PEI 25 kDa linear, Polyscience, Warrington, Calif.). Four to six hours later, the medium was replaced with fresh medium containing 1 µg/mL of doxycycline and 50 µg/mL of cumate. 48 h later the medium was harvested by ultracentrifugation on a 20% sucrose gradient. The LV pellets were resuspended into a small volume (about 500 µl) of DMEM (Dulbecco's Modified Eagle's Medium) supplemented with 10% FBS and transferred at –80° C. until needed. Stable producers were generated by transducing 293SF-PacIV with the concentrated LV in the presence of 8 µg/ml of polybrene (Hexadimethrine Bromide, Sigma). The next day, the medium was replaced with fresh one. The cells were expended and transferred into 125 ml shake flasks. When the cell density reached $1.0 \times 10^6$ cell/ml, the production of LV was initiated by adding 1 µg/mL of doxycycline and 50 µg/mL of cumate. After 48 h the supernatant was collected daily for four days and the LV was concentrated by ultracentrifugation on a 20% sucrose gradient and resuspended into 1 ml of DMEM supplemented with 10% FBS and stored at –80° C. until needed. The number of physical particles (particles/ml) of LV-CMV-GFP and LV-ΔUSEx3-GFP was determined by measuring the quantity of p24 by Enzyme Linked ImmunoSorbent Assay (ELISA) as described [34, 37]. The infectious titer (transducting units [TU]/ml) of LV-CMV-GFP was determined by flow cytometry by measuring the % of cells expressing GFP after transduction of 293 cells [37]. The infectious titer (TU/ml) of LV-ΔUSE-GFP was extrapolated from its titer of physical particles.

Cell Culture Experiments using Lentiviral Vectors

Actively dividing C2C12 myoblasts in DMEM supplemented with 10% FBS were infected with concentrated stock of LV-CMV-GFP or LV-ΔUSE×3-GFP at a multiplicity of infection (MOI) of 750 and 3750 TU per cell using standard protocols as described above. After 24 h, the medium was replaced with fresh one and the cells were kept in culture for three weeks by replacing the medium every two to three days. At selected time points, the level of GFP expression in the cell population was determined by flow cytometry using standard procedures. After 19 days of culture, equal numbers of myoblasts were differentiated into myotubes by replacing the medium with DMEM supplemented with 2% horse serum as described above. 7 days later, phase contrast and fluorescence pictures of the myotubes were take using a Leica DMIL Fluorescence microscope equipped with a CCD camera (Retiga, 2000R QImaging).

Statistical Analysis

The data are expressed as the mean±SEM. The data were analyzed using an analysis of variance (ANOVA) followed by the Fisher's LSD procedure to compare the means. Some means were also compared with each other using a Student's t-Test. Statistical significance was set at $P<0.05$.

Results:

Description of the Constructs

Referring to FIG. 1, constructs were made by fusing one to five copies of USE or one to four copies of ΔUSE upstream of the minimal promoter (region –95 to +56) of the human TnISlow gene. Some of the ΔUSE constructs (ΔUSE×1(–) and ΔUSE×2(–)) were tested in the two possible orientations. FIG. 1C provides the nucleotide sequence (SEQ ID NO: 17) for the USE×1 construct. The sequence of USE (region –1035 to –874) is in italics and underlined. The sequence of the minimal TnISlow promoter (region –95 to +56) is bold and underlined. The numbers above the sequence correspond to the nucleotide number of the genetic elements derived from the human TnISlow gene. Number 1+ corresponds to the transcription start site.

Because three copies of the IRE enhancer of the quail TnIFast gene has been shown to confer excellent muscle-specific expression in vivo [26], constructs containing the minimal quail TnIFast promoter linked to three copies of the IRE (FIG. 2) were also tested for comparison. These IRE enhancers were also tested in the two possible orientations. Two constructs were made by combining genetic elements derived from the quail TnIFast gene (TnIF(Im–) and TnIF (Im+) and one from the human MCK gene. TnIF(Im–) differs from TnIF(Im+) because of the orientation of the three copies of IRE. The strength of these constructs was compared to the CMV early enhancer/minimal promoter [38] and to the hybrid CMV enhancer and β-actin (CB) promoter, also known as CAG [39] (FIG. 2). Comparisons were also made with the short (1.3-kb in length) muscle creatine kinase enhancer/promoter (MCK) (FIG. 2). The later construct has been shown to confer muscle specific expression in vivo after gene transfer using E1-deleted adenovirus [27, 40]. In FIG. 2, the numbers below the genetic elements indicate their position relative to the transcription start site in the original gene.

Because the presence of an intron can improve the level and stability of gene expression in vivo [41-43], a small intron of 100-bp was inserted after the transcription start sites of each of the constructs, except for CB and MCK. The CB construct possesses already an intron of 1.6-kb whereas the MCK does not have one. The intron that was used is derived from the 16/19S late mRNA of SV40 [44]. However, because the original intron contained within its sequence an ATG that could initiate translation if it is not completely spliced out, this ATG was replaced with the sequence ATA to prevent formation of a fusion protein. All these constructs were cloned into same plasmid backbone, encoding the gene for β-galactosidase (β-gal), which was used as gene reporter.

Strength of Constructs in Cell Culture

Figure 3A:
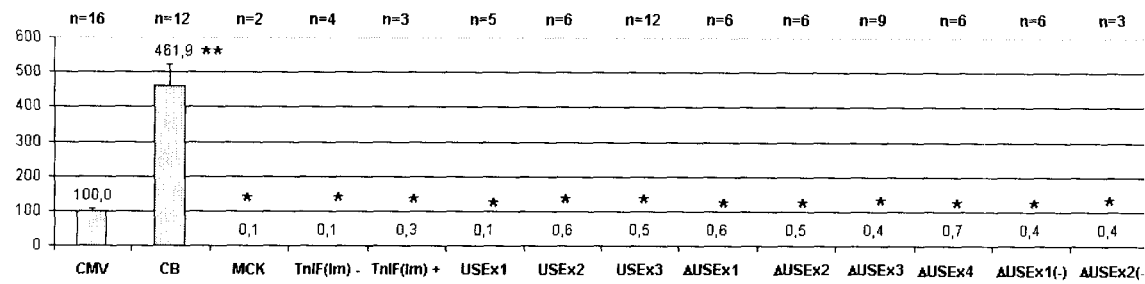
FIG. 3 depicts graphs indicating strength of constructs in culture of A) non-muscle cells (293A), B) C2C12 myoblasts, and C) C2C12 myotubes transfected with plasmids encoding β-gal under the control of the constructs described in FIGS. 1 and 2.
Figure 3B:
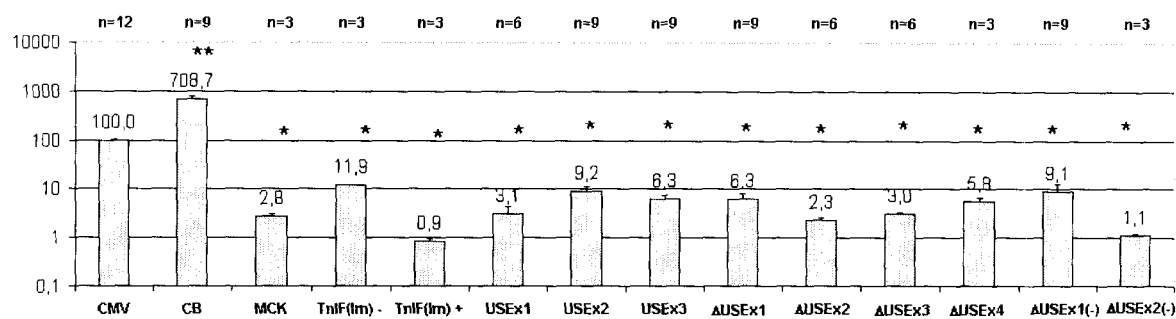
Figure 3C:
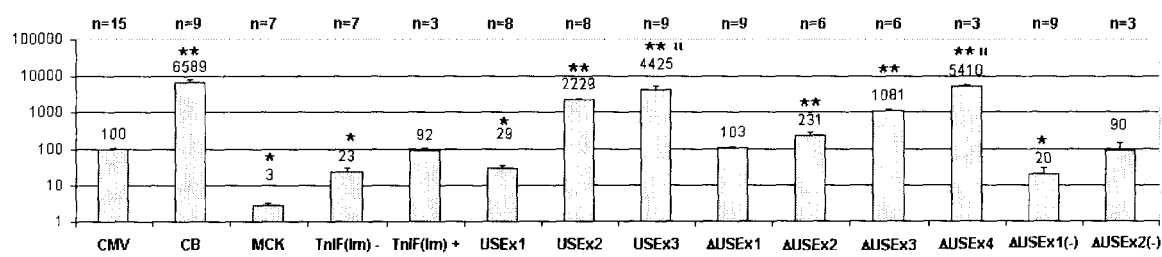

The strengths of constructs described in FIGS. 1 and 2 were first compared by transient transfection in non-muscle cells (293 cells), actively dividing C2C12 myoblasts and differentiated C2C12 myotubes. Referring to FIG. 3, one day after transfection, some myoblasts were transferred into differentiation medium to promote the formation of myotubes (C). Two days (293A and myoblasts) or 11 days after transfection (myotubes) the cell were lysed and the β-gal activity was measured by luminometry. The expression of β-gal was also monitored using light microscopy by staining the cells with X-gal. The β-gal activity was normalized to the value of CMV, which was arbitrary set to 100. In addition, the β-gal plasmids were spiked with an equivalent amount of plasmid encoding the secreted alkaline phosphatase (SEAP) regulated by the CMV enhancer/promoter. The SEAP activity, which was measured in the cell culture supernatant at the time of cell lysis, was used to normalize the transfection efficiency. In FIG. 3, the data are the means±SEM; for each construct, the number (N) of different samples analyzed is indicated; * value is significantly smaller than CMV;  value is significantly higher than CMV; '" value is not different than CB.

The CB construct was the best construct tested in 293 cells. Its activity was 4.6 times higher than CMV. All the other constructs tested in this cell line bestowed a very weak activity that corresponded to 0.1 to 0.6% of the activity of CMV (FIG. 3A). In dividing myoblasts, CB was also the best construct. It was seven times stronger than CMV. Although all the other constructs were significantly weaker than CMV, their relative activity in comparison to CMV was higher than in 293A cells. In myoblasts, the best three muscle-specific constructs were TnIF(Im), USE×2 and ΔUSE×2 with an activity around 10% of CMV. In differentiated myotubes, the activity of CB was 66 times higher than CMV. More importantly the activity of two constructs (USE×3, and ΔUSE×4) was equivalent to CB. Although weaker than CB, three other constructs were also stronger than CMV. Hence, the activity of USE×2, ΔUSE×3 and ΔUSE×2 were 22, 10 and 2.3 times better than CMV. In differentiated myotubes, the strength of a particular construct was higher if more copies of USE and ΔUSE were present. For the same number of copies, the activity of USE was stronger than the activity of ΔUSE and IRE, the latter being the weakest. Constructs containing USE×3 were about forty-eight times stronger than constructs containing IRE×3. The strength of the ΔUSE, and IRE was also better when they were placed in a natural orientation.

Figure 4:
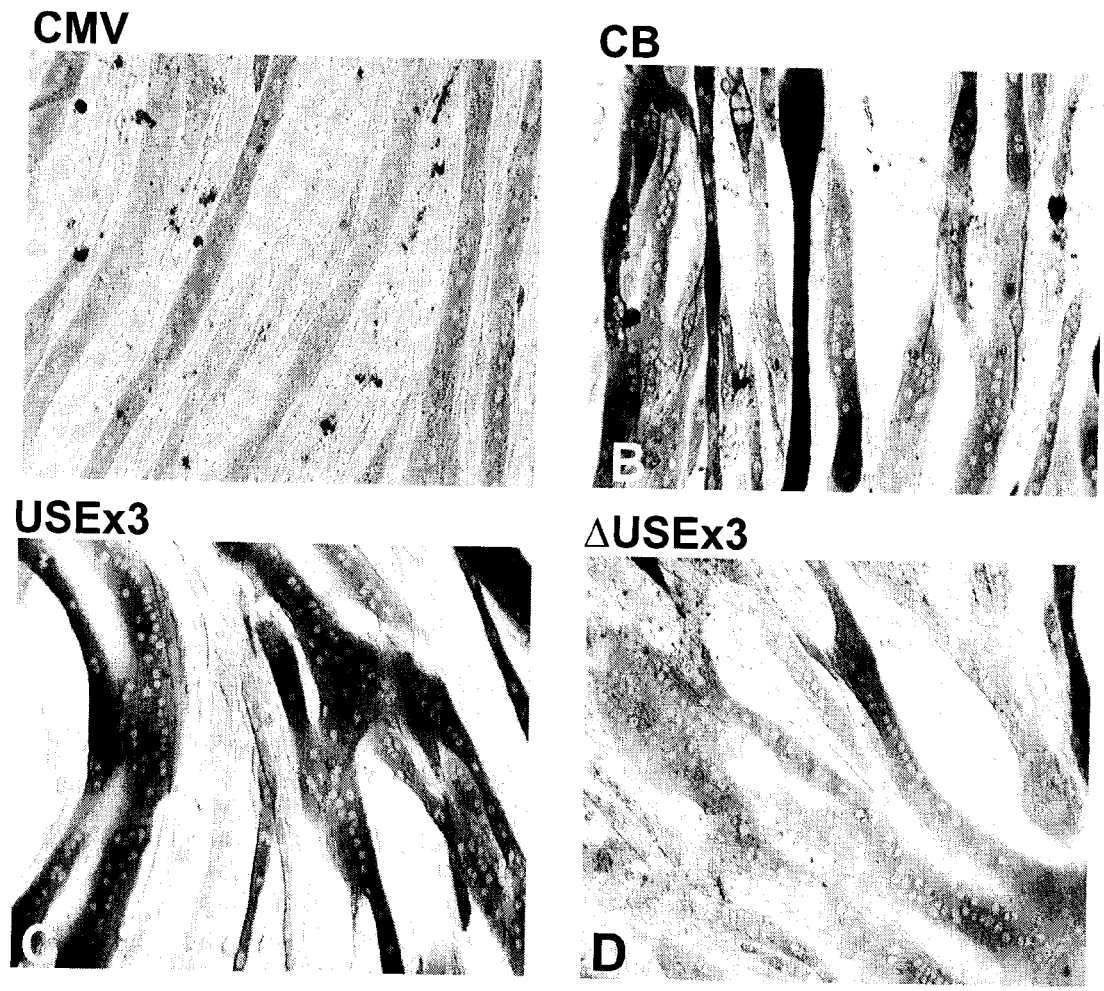
FIG. 4 depicts distribution of β-gal in culture of myotubes.

The expression of β-gal was also analyzed by histochemistry in differentiated myotubes. One day after transfection, myoblasts were transferred into differentiating medium and processes for β-gal histochemistry 10 days later. Representative micrographs are presented in FIG. 4 demonstrating that cultures of differentiated C2C12 cells, transfected with some of the best constructs of the present invention contained numerous large polynucleated myotubes expressing large amount of β-gal. In FIG. 4, the β-gal positive myotubes are a darker shade of gray.

Figure 5A:
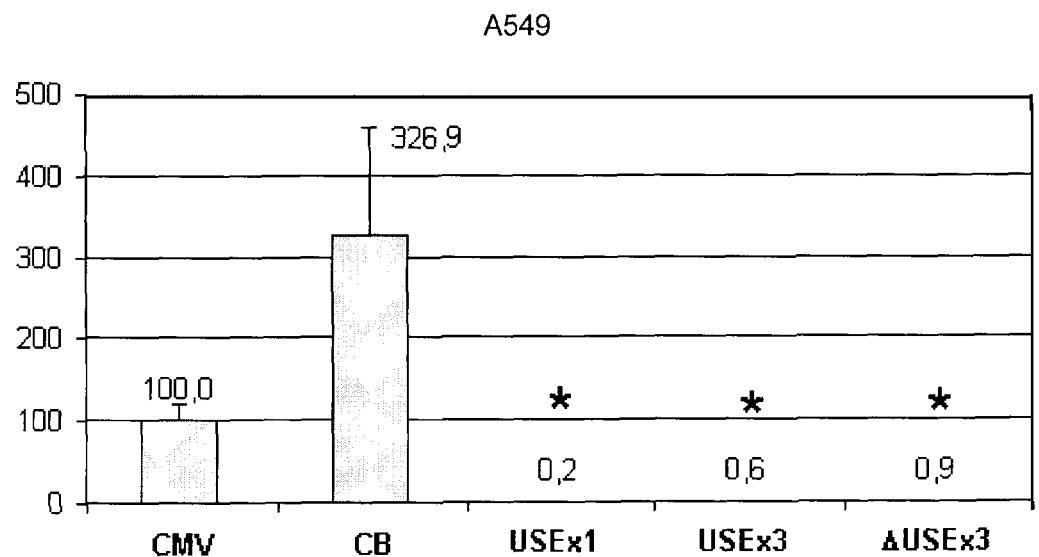
FIG. 5 depicts graphs indicating strength of USE×3 and ΔUSE×3 in non-muscle cells: A) A549, and B) HeLa.
Figure 5B:
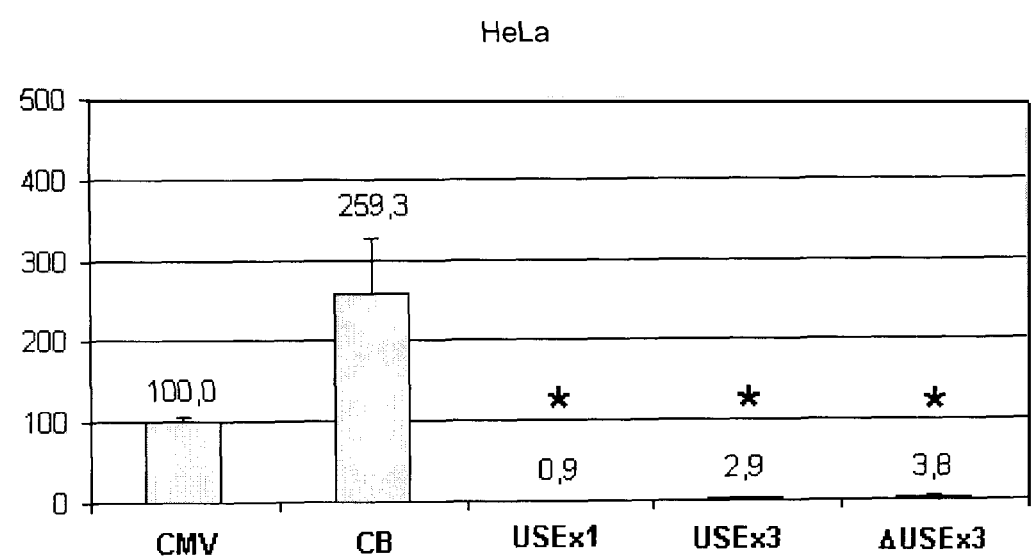

Referring to FIG. 5, the specificity of two constructs (USE×3 and ΔUSE×3) was further evaluated by transient transfection in human lung carcinoma! cells (A549) (FIG. 5A) and in human cervical cancer cells (HeLa) (FIG. 5B). These experiments were performed as described above using SEAP to normalize the transfection efficiency, and as control, the cells were transfected with the USE×1, CMV and CB constructs. Two days after transfection, the cells were lysed and β-gal activity was measured by luminometry. The β-gal activity was normalized to the value of CMV, which was set arbitrary to 100. The data in FIG. 5 are the means±SEM. For each construct, 6 different samples were analyzed. The * in FIG. 5 means that the value is significantly smaller than CMV. In both cell lines, the strength of ΔUSE×3 and USE×3 was comparable with each other and significantly weaker than CMV (FIG. 5).

Strength of the Constructs in Mouse Muscle

Figure 6A:
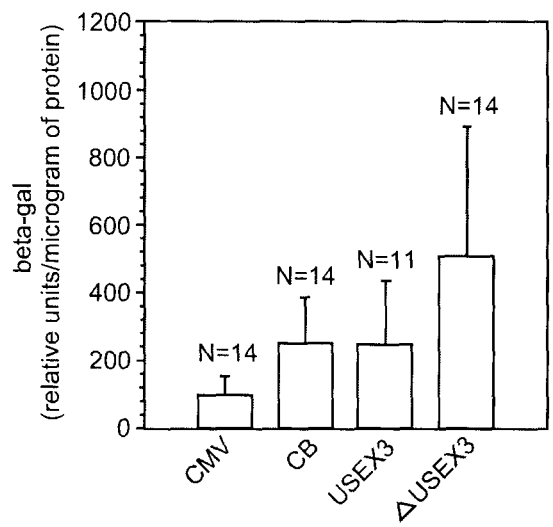
FIG. 6 depicts graphs indicating strength of USE×3 and ΔUSE×3 in mouse muscle in vivo: A) relative amount of β-gal produced per muscles, and B) number of β-gal positive fibers.
Figure 6B:
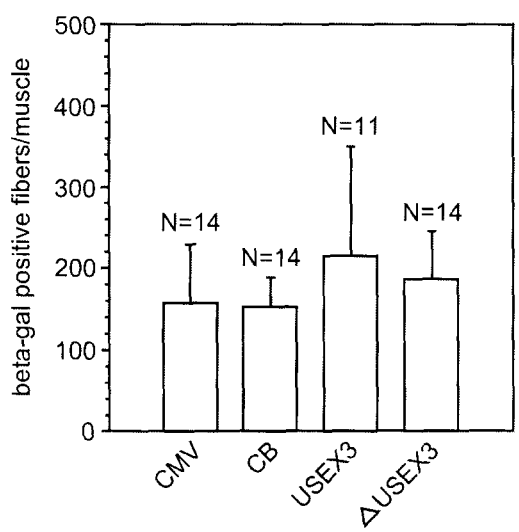
Figure 7:
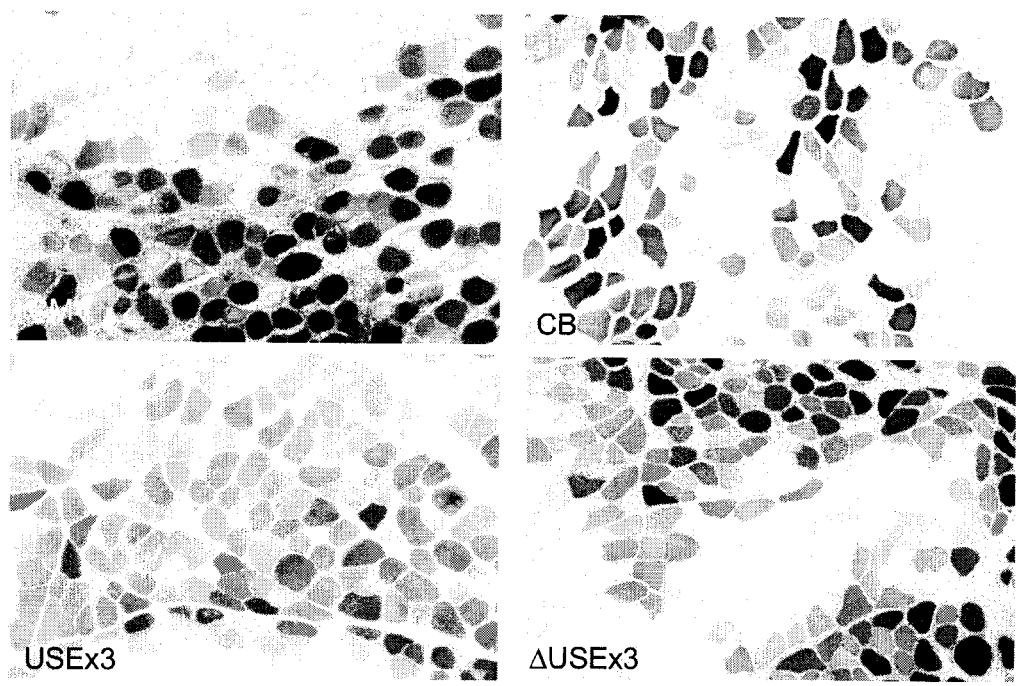
FIG. 7 depicts the distribution of β-gal in muscle after injection of plasmids expressing β gal under the control of the indicated constructs. The tibialis anterior (TA) muscle of CD1 mice was injected with plasmids followed by electroporation to increase transduction. Ten days later, the mice were sacrificed and the TA was removed. Cross-sections of the injected TA were processed for histochemistry to visualize β-gal. The transduced muscle fibers (the fibers expressing β-gal) are dark.

The activity of USE×3 and ΔUSE×3 in mouse muscle was tested in vivo. The tibialis anterior (TA) of adult normal mice was injected with plasmids encoding β-gal regulated by USE×3 or by ΔUSE×3. This was followed by the application of pulses of electric current (electrotransfer) as described previously [32]. Electrotransfer is known to dramatically increase the transduction efficiency of naked DNA in muscle [45-47]. As control, muscles were also injected in a similar manner with plasmids carrying β-gal regulated by CB or CMV. At 10 days post injection, the level of β-gal in the injected muscle was determined by luminometry (FIG. 6A). Sections of injected muscles were also processed for β-gal histochemistry to reveal the number of transduced (β-gal positive) muscle fibers (FIG. 6B). Representative pictures of stained muscle sections are shown in FIG. 7. In FIG. 6, the data are the means±SEM, and for each construct, the number (N) of different muscles analyzed is indicated. There was no significant difference between the amount of β-gal produced and the number of transduced fibers following electrotransfer of the four constructs tested (CMV, CB, USE×3 and ΔUSE×3). Overall, the transduction efficiency was high because an average of 150 to 200 fibers was positive for β-gal, which represents 8 to 10% of the total number of fibers in the TA. The fact that USE×3 and ΔUSE×3 were equally active in the TA, which consists primarily of fast-twitch muscle fibers, indicates that in the context of electrotransfer of naked DNA, these two constructs were functional in fast-twitch muscle fibers.

Figure 8:
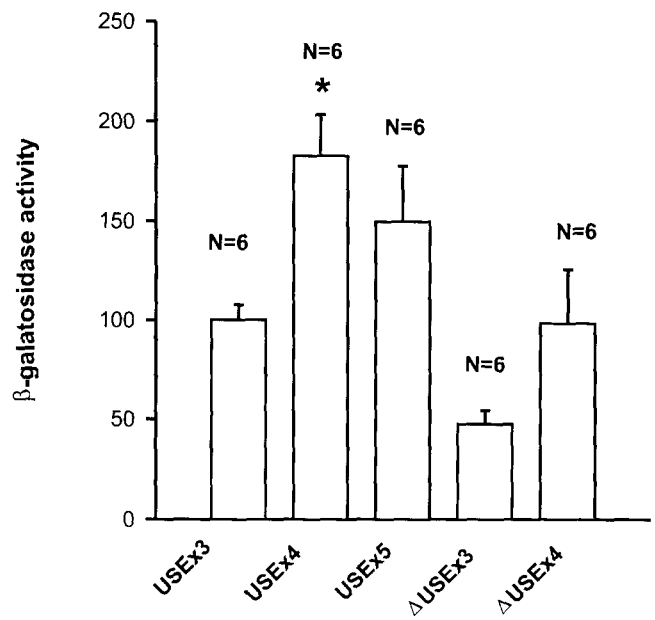
FIG. 8 depicts a graph indicating strength of constructs in culture of myotubes transfected with plasmid encoding β-gal regulated by constructs described in FIG. 1. N=number of samples; * value greater than USE×3 ($p<0.01$).

To verify if it is possible to obtain constructs stronger than USE×3 in muscle cells, we generated USE×4 and USE×5, which contain four and five copies of USE respectively (FIG. 1). The strength of these constructs was then tested in cultures of myotubes using plasmids encoding β-gal as described previously (FIG. 8). For comparison, the cells were also transfected with plasmids carrying USE×3, ΔUSE×3 and ΔUSE×4. The data showed that USE×4 was stronger than USE×3, ΔUSE×3 and ΔUSE×4. In the same experiment, the strength of USE×5 was not better than the strength of USE×4. Taken together, these data showed that the optimal strength is obtained with four copies of USE and that no additional benefit incurred by using five copies of USE.

Figure 9:
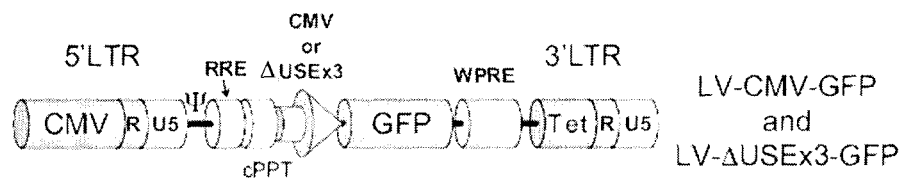
FIG. 9 depicts the structure of the two lentiviral vectors that were used to express the green fluorescent protein (GFP) regulated by CMV or regulated by ΔUSE×3.
Figure 10:
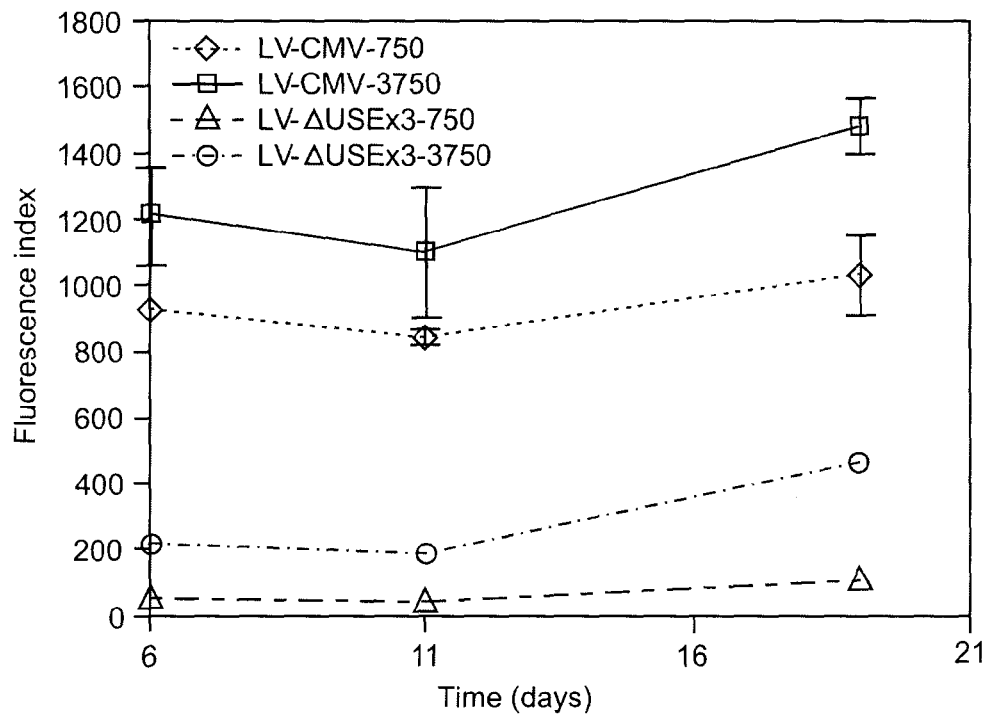
FIG. 10 depicts a graph of the strength and stability of GFP in culture of actively dividing myoblasts infected with LV-CMV-GFP and LV-ΔUSE×3-GFP. The amount of LV added per cells (750 or 3750 transducing units/cell) is indicated. The expression of GFP was monitored at day 6, 11 and 19 after infection by flow cytometry. The fluorescence index (percentage of cells expressing GFP multiplied by the intensity of fluorescence) is shown.
Figure 11:
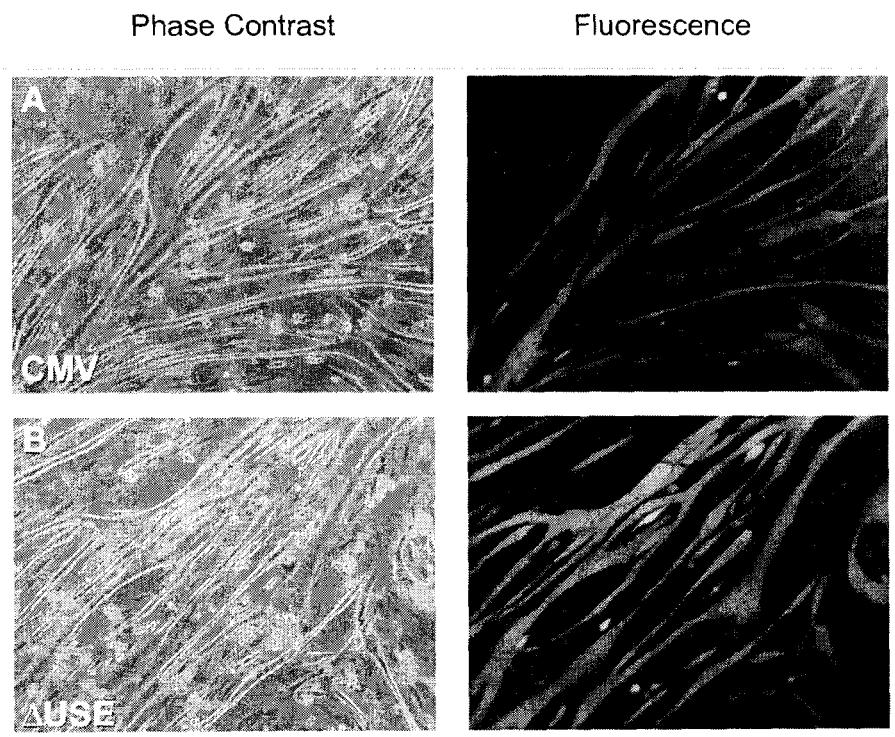
FIG. 11 depicts the expression of GFP in myotubes that were infected with LV-CMV-GFP (A) or with LV-ΔUSE×3-GFP (B). Phase contrast and fluorescence images of the same myotubes are shown. For this experiment, stably transduced myoblasts at an MOI of 3750 with the LV described in FIG. 9 were differentiated for 7 days into myotubes.

Vectors derived from lentivirus (lentiviral vectors, LV) are becoming increasingly popular for various gene therapy applications, because of their ability to stably integrate their genome into the chromosomes of dividing and non-dividing cells (reviewed in [48-50]. To investigate if the constructs described in this study were functional when carried by LV, we generated a LV expressing the green fluorescent protein (GFP) regulated by ΔUSE×3 (FIG. 9). As control, we also constructed a comparable LV expressing GFP regulated by CMV. The ability of these LV to stably deliver GFP in culture of actively dividing myoblasts was studied by infecting such cultures with different quantities of LV (750 or 3750 transducing units (TU)/cell). GFP expression in cultures of non-differentiated myoblasts was stronger with CMV compare to ΔUSE×3 (FIG. 10). Expression of GFP was stable for at least 19 days using both LV. Cultures of myoblasts infected with the higher titer (3750 TU/cells) were then differentiated into myotubes (FIG. 11). After differentiation, the GFP expression level, as visualized under the fluorescent microscope, was higher in the myotubes transduced with the LV carrying ΔUSE×3 indicating that the strength of this construct was better in CMV.

Discussion

Muscle-specific and unexpectedly very powerful constructs have been generated by multimerizing the USE and ΔUSE in front of the minimal TnISlow promoter. The strength of these constructs was compared the CMV enhancer/promoter and to the hybrid CMV enhancer/β-actin promoter (CB, also known as CAG). The data is in agreement with previous studies [16, 39, 51, 52] that showed that CB is a very strong promoter, as its strength was better than CMV in 293 cells, myoblasts and myotubes. The difference between CMV and CB in A549 and HeLa cells was not significant. In differentiated myotubes, CB was significantly stronger than CMV and four constructs (USE×3, USE×4, USE×5 and ΔUSE4) were comparable to CB. Although weaker than CB, two constructs of the present invention (USE×2 and ΔUSE× 3) were also better than CMV. The most powerful constructs was USE×4. In differentiated myotubes, the strength of the TnISlow constructs increased with the number of copies of USE and ΔUSE present. However, in the case of USE, the optimal strength was obtained with four copies of USE and that no additional benefit incurred by using five copies of USE enhancer. Constructs made with three copies of the IRE enhancers upstream of the TnIFast minimal promoter were significantly weaker than those derived from the TnISlow gene. The orientation of the ΔUSE and IRE also has an effect because the strength of a particular construct was better when the orientation of these enhancers was the same as the one found in nature.

One of the best muscle-specific regulatory elements described in the literature is the artificial SpC5-12 construct that was generated by the random assembly of several myogenic regulatory elements. In culture of chicken myotubes, this construct is 6 times stronger than CMV [53]. The strength of a construct derived from the muscle-specific skeletal α-actin promoter was reported to be comparable to CMV in culture of muscle cells [54]. Several muscle-specific constructs were engineered by combining the enhancers and the minimal promoter elements of MCK. The best of these constructs, referred to as CK6, has an activity corresponding to 8% of CMV in muscle cultures [18]. The same group showed that CK2, a construct similar to our short MCK construct, possesses an activity corresponding to 1.3% of CMV, a value close to the one (3%) we obtained. Other strong muscle-specific constructs made by combining the skeletal α-actin promoter with the β-enolase or the MCK enhancer have been described [55]. In muscle cell cultures, these constructs were 2 to 6 times better than the long terminal repeats (LTR) of Rous sarcoma virus (RSV). Chimeric constructs made by splicing together the myosin light chain enhancer with the MCK, the myosin heavy chain, or the myosin light chain promoters were demonstrated to be as active as the SV40 early promoter in culture of myotubes [56]. Although the RSV LTR and SV40 early promoter can provide high transcription level, they are not stronger than CMV in muscle cells [51, 57]. Although it is difficult to compare results obtained from different laboratories under different conditions, the fact that some of the constructs of the present invention were 40 times to 60 times better than CMV, and that none of the muscle-specific constructs reported in the literature were as strong comparatively to CMV, RSV and SV40, indicates that TnISlow constructs of the present invention may be among the most active muscle-specific enhancer/promoter combinations described so far.

The TnISlow constructs of the present invention are muscle-specific because they are very active in differentiated culture of myotubes (C2C12) and poorly active in non-muscle cells (293 cells). They were also poorly inactive in undifferentiated cultures of myoblasts. Additional studies using USE×3 and ΔUSE×3 in two non-muscle cell lines (HeLa, A549) confirmed the muscle specificity of these constructs, as low activity was observed. These data indicate that multimerization of USE and ΔUSE did not alter significantly their tissue specificity. A single copy of USE confers preferential expression in slow-twitch muscle fibers, whereas one copy of ΔUSE can provide efficient expression in slow-twitch as well as in fast-twitch muscle fibers [22-24]. If this property of USE and ΔUSE is preserved after multimerization, constructs containing several copies of ΔUSE should be more advantageous for gene therapy, because expression would occur in every skeletal muscle fibers of the body irrespective of their type. According to the electrotransfer data, the activity of USE×3 and ΔUSE×3 were comparatively strong in the TA muscle of normal mouse. Because the TA consists primarily of fast-twitch muscle fibers, the data indicate that the USE×3 and ΔUSE×3 are active in fast-twitch muscle fiber. Multimerization of USE may have thus modified its fiber-type specificity, because USE×3 is active in fast-twitch muscle fibers. However it cannot be ruled out that electrotransfer is a relatively insensitive method that is unable to measure subtle variation of promoter activity in vivo. This could explain why the activities of the four constructs tested in vivo (CMV, CB, USE×3 and ΔUSE×3) using electrotransfer were comparable, although their activities were different in cell culture. Testing these constructs using viral vectors could provide more accurate and relevant information for gene therapy application. Indeed, using a gutless adenovirus vector expressing dystrophin, it has been previously shown that the dystrophin expression level was significantly stronger with CB compared with CMV in cell culture and in mouse muscle in vivo [52].

Another important characteristic of the TnISlow constructs of the present invention is their small size, less than about 600 bp. They are thus sufficiently small to drive muscle-specific expression of transgenes carried by viral vectors such as recombinant AAV, whose transport capacity is very limited (around 4.7 kb).

We have also demonstrated the functionality of one construct (ΔUSE×3) in the context of lentiviral vectors. In comparison to CMV, this construct was weak in non-differentiated myoblasts and strong in differentiated myotubes, thus demonstrating its strength and specificity for muscle. As expected, after transduction of LV, the level of GFP expression did not decrease after three weeks of culture indicating that both expression cassettes were stably integrated into the chromosomes of the myoblasts.

Thus, strong and muscle-specific expression can be obtained by using constructs of the present invention containing multimers of USE and/or ΔUSE enhancers. The surprising strength of these constructs and their relatively small size should make them very useful for gene therapy.

REFERENCES

The disclosures of the following references are incorporated herein by reference in their entirety.

1. Ratanamart, J. and Shaw, J. A. (2006). Plasmid-mediated muscle-targeted gene therapy for circulating therapeutic protein replacement: a tale of the tortoise and the hare? Curr. Gene Ther. 6: 93-110.
2. Goldspink, G. (2003). Skeletal muscle as an artificial endocrine tissue. Best. Pract. Res. Clin. Endocrinol. Metab 17: 211-222.
3. Lu, Q. L., Bou-Gharios, G., and Partridge, T. A. (2003). Non-viral gene delivery in skeletal muscle: a protein factory. Gene Ther. 10: 131-142.
4. Wang, L. and Herzog, R. W. (2005). AAV-mediated gene transfer for treatment of hemophilia. Curr. Gene Ther. 5: 349-360.
5. Sun, B. et al. (2005). Correction of glycogen storage disease type II by an adeno-associated virus vector containing a muscle-specific promoter. Mol. Ther. 11: 889-898.
6. Takahashi, H. et al. (2002). Long-term systemic therapy of Fabry disease in a knockout mouse by adeno-associated virus-mediated muscle-directed gene transfer. Proc. Natl. Acad. Sci. U.S.A 99: 13777-13782.
7. Tripathy, S. K. et al. (1996). Long-term expression of erythropoietin in the systemic circulation of mice after intramuscular injection of a plasmid DNA vector. Proc. Natl. Acad. Sci. U.S.A 93: 10876-10880.
8. Lu, Y. et al. (2006). Therapeutic level of functional human alpha 1 antitrypsin (hAAT) secreted from murine muscle transduced by adeno-associated virus (rAAV1) vector. J. Gene Med. 8: 730-735.
9. Athanasopoulos, T. et al. (2000). Intramuscular injection of a plasmid vector expressing human apolipoprotein E limits progression of xanthoma and aortic atheroma in apoE-deficient mice. Hum. Mol. Genet. 9: 2545-2551.
10. Harris, J. D. et al. (2002). Inhibition of atherosclerosis in apolipoprotein-E-deficient mice following muscle transduction with adeno-associated virus vectors encoding human apolipoprotein-E. Gene Ther. 9: 21-29.
11. Chamberlain, J. S. (2002). Gene therapy of muscular dystrophy. Hum. Mol. Genet. 11: 2355-2362.
12. Stedman, H. H. (2001). Molecular approaches to therapy for Duchenne and limb-girdle muscular dystrophy. Curr. Opin. Mol. Ther. 3: 350-356.
13. Deconinck, N., Ragot, T., Marechal, G., Perricaudet, M., and Gillis, J. M. (1996). Functional protection of dystrophic mouse (mdx) muscles after adenovirus-mediated transfer of a dystrophin minigene. Proc. Natl. Acad. Sci. U.S.A 93: 3570-3574.
14. Yang, Y., Haecker, S. E., Su, Q., and Wilson, J. M. (1996). Immunology of gene therapy with adenoviral vectors in mouse skeletal muscle. Hum. Mol. Genet. 5: 1703-1712.
15. Acsadi, G. et al. (1996). Dystrophin expression in muscles of mdx mice after adenovirus-mediated in vivo gene transfer. Hum. Gene Ther. 7: 129-140.
16. Ishii, A. et al. (1999). Effective adenovirus-mediated gene expression in adult murine skeletal muscle. Muscle Nerve 22: 592-599.
17. Pastore, L. et al. (1999). Use of a liver-specific promoter reduces immune response to the transgene in adenoviral vectors. Hum. Gene Ther. 10: 1773-1781.
18. Hauser, M. A. et al. (2000). Analysis of muscle creatine kinase regulatory elements in recombinant adenoviral vectors. Mol. Ther. 2: 16-25.
19. Hartigan-O'Connor, D., Kirk, C. J., Crawford, R., Mule, J. J., and Chamberlain, J. S. (2001). Immune evasion by muscle-specific gene expression in dystrophic muscle. Mol. Ther. 4: 525-533.
20. Cordier, L. et al. (2001). Muscle-specific promoters may be necessary for adeno-associated virus-mediated gene transfer in the treatment of muscular dystrophies. Hum. Gene Ther. 12: 205-215.
21. Hagstrom, J. N. et al. (2000). Improved muscle-derived expression of human coagulation factor IX from a skeletal actin/CMV hybrid enhancer/promoter. Blood 95: 2536-2542.
22. Corin, S. J., Levitt, L. K., O'Mahoney, J. V., Joya, J. E., Hardeman, E. C., and Wade, R. (1995). Delineation of a slow-twitch-myofiber-specific transcriptional element by using in vivo somatic gene transfer. Proc. Natl. Acad. Sci. U.S.A 92: 6185-6189.
23. Nakayama, M., Stauffer, J., Cheng, J., Banerjee-Basu, S., Wawrousek, E., and Buonanno, A. (1996). Common core sequences are found in skeletal muscle slow- and fast-fiber-type-specific regulatory elements. Mol. Cell Biol. 16: 2408-2417.
24. Calvo, S., Vullhorst, D., Venepally, P., Cheng, J., Karavanova, I., and Buonanno, A. (2001). Molecular dissection of DNA sequences and factors involved in slow muscle-specific transcription. Mol. Cell Biol. 21: 8490-8503.
25. Yutzey, K. E., Kline, R. L., and Konieczny, S. F. (1989). An internal regulatory element controls troponin I gene expression. Mol. Cell Biol. 9: 1397-1405.
26. Hallauer, P. L. and Hastings, K. E. (2002). TnIfast IRE enhancer: multistep developmental regulation during skeletal muscle fiber type differentiation. Dev. Dyn. 224: 422-431.
27. Larochelle, N. et al. (2002). The short MCK1350 promoter/enhancer allows for sufficient dystrophin expression in skeletal muscles of mdx mice. Biochem. Biophys. Res. Commun. 292: 626-631.
28. Hallauer, P. L., Bradshaw, H. L., and Hastings, K. E. (1993). Complex fiber-type-specific expression of fast skeletal muscle troponin I gene constructs in transgenic mice. Development 119: 691-701.
29. Yaffe, D. and Saxel, O. (1977). Serial passaging and differentiation of myogenic cells isolated from dystrophic mouse muscle. Nature 270: 725-727.
30. Gaillet, B. et al. (2007). High-Level Recombinant Protein Production in CHO Cells Using an Adenoviral Vector and the Cumate Gene-Switch. Biotechnol. Prog. 23: 200-209.
31. Massie, B. et al. (1998). New adenovirus vectors for protein production and gene transfer. Cytotechnology 28: 53-64.
32. Molnar, M. J. et al. (2004). Factors influencing the efficacy, longevity, and safety of electroporation-assisted plasmid-based gene transfer into mouse muscles. Mol. Ther. 10: 447-455.
33. Acsadi, G. et al. (1994). A differential efficiency of adenovirus-mediated in vivo gene transfer into skeletal muscle cells of different maturity. Hum. Mol. Genet. 3: 579-584.
34. Broussau, S. et al. (2008). Inducible Packaging Cells for Large-scale Production of Lentiviral Vectors in Serum-free Suspension Culture. Mol. Ther. 16: 500-507.
35. Miyoshi, H., Blomer, U., Takahashi, M., Gage, F. H., and Verma, I. M. (1998). Development of a self-inactivating lentivirus vector. J. Virol. 72: 8150-8157.
36. Vigna, E. et al. (2002). Robust and efficient regulation of transgene expression in vivo by improved tetracycline-dependent lentiviral vectors. Mol. Ther. 5: 252-261.

37. Gilbert, R., Broussau, S., and Massie, B. (2007). Protein production using lentiviral vectors. In *Expression systems*. (M. R. Dyson and Y. Durocher, Eds.), pp. 241-258, Scion,
38. Boshart, M., Weber, F., Jahn, G., Dorsch-Hasler, K., Fleckenstein, B., and Schaffner, W. (1985). A very strong enhancer is located upstream of an immediate early gene of human cytomegalovirus. *Cell* 41: 521-530.
39. Niwa, H., Yamamura, K., and Miyazaki, J. (1991). Efficient selection for high-expression transfectants with a novel eukaryotic vector. *Gene* 108: 193-199.
40. Larochelle, N. et al. (1997). Efficient muscle-specific transgene expression after adenovirus-mediated gene transfer in mice using a 1.35 kb muscle creatine kinase promoter/enhancer. *Gene Ther.* 4: 465-472.
41. Brinster, R. L., Allen, J. M., Behringer, R. R., Gelinas, R. E., and Palmiter, R. D. (1988). Introns increase transcriptional efficiency in transgenic mice. *Proc. Natl. Acad. Sci. U.S.A* 85: 836-840.
42. Palmiter, R. D., Sandgren, E. P., Avarbock, M. R., Allen, D. D., and Brinster, R. L. (1991). Heterologous introns can enhance expression of transgenes in mice. *Proc. Natl. Acad. Sci. U.S.A* 88: 478-482.
43. Furger, A., O'Sullivan, J. M., Binnie, A., Lee, B. A., and Proudfoot, N. J. (2002). Promoter proximal splice sites enhance transcription. *Genes Dev.* 16: 2792-2799.
44. Okayama, H. and Berg, P. (1983). A cDNA cloning vector that permits expression of cDNA inserts in mammalian cells. *Mol. Cell Biol.* 3: 280-289.
45. Mir, L. M. et al. (1999). High-efficiency gene transfer into skeletal muscle mediated by electric pulses. *Proc. Natl. Acad. Sci. U.S.A* 96: 4262-4267.
46. Mathiesen, I. (1999). Electropermeabilization of skeletal muscle enhances gene transfer in vivo. *Gene Ther.* 6: 508-514.
47. Aihara, H. and Miyazaki, J. (1998). Gene transfer into muscle by electroporation in vivo. *Nat. Biotechnol.* 16: 867-870.
48. Vigna, E. and Naldini, L. (2000). Lentiviral vectors: excellent tools for experimental gene transfer and promising candidates for gene therapy. *J. Gene Med.* 2: 308-316.
49. Lever, A. M., Strappe, P. M., and Zhao, J. (2004). Lentiviral vectors. *J. Biomed. Sci.* 11: 439-449.
50. Sinn, P. L., Sauter, S. L., and McCray, P. B., Jr. (2005). Gene therapy progress and prospects: development of improved lentiviral and retroviral vectors—design, biosafety, and production. *Gene Ther.* 12: 1089-1098.
51. Xu, Z. L., Mizuguchi, H., Ishii-Watabe, A., Uchida, E., Mayumi, T., and Hayakawa, T. (2001). Optimization of transcriptional regulatory elements for constructing plasmid vectors. *Gene* 272: 149-156.
52. Gilbert, R., Liu, A., Petrof, B., Nalbantoglu, J., and Karpati, G. (2002). Improved performance of a fully gutted adenovirus vector containing two full-length dystrophin cDNAs regulated by a strong promoter. *Mol. Ther.* 6: 501-509.
53. Li, X., Eastman, E. M., Schwartz, R. J., and Draghia-Akli, R. (1999). Synthetic muscle promoters: activities exceeding naturally occurring regulatory sequences. *Nat. Biotechnol.* 17: 241-245.
54. Li, S. et al. (1999). Increased level and duration of expression in muscle by co-expression of a transactivator using plasmid systems. *Gene Ther.* 6: 2005-2011.
55. Frauli, M., Ribault, S., Neuville, P., Auge, F., and Calenda, V. (2003). Adenoviral-mediated skeletal muscle transcriptional targeting using chimeric tissue-specific promoters. *Med. Sci. Monit.* 9: BR78-BR84.
56. Skarli, M., Kiri, A., Vrbova, G., Lee, C. A., and Goldspink, G. (1998). Myosin regulatory elements as vectors for gene transfer by intramuscular injection. *Gene Ther.* 5: 514-520.
57. Danko, I. et al. (1997). High expression of naked plasmid DNA in muscles of young rodents. *Hum. Mol. Genet.* 6: 1435-1443.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A construct comprising two or more enhancers from a slow troponin I gene fused in line and operably linked to a muscle cell specific promoter, and a nucleotide sequence of interest, wherein each enhancer comprises the nucleotide sequence as set forth in nucleotides 152 to 218 of SEQ ID NO:17 or as set forth in nucleotides 57-218 of SEQ ID NO: 17, and wherein the construct ensures tissue-specific expression of the nucleotide of interest in muscle cells.

2. The construct of claim 1, wherein the two or more enhancers are upstream of the promoter.

3. The construct of claim 1, wherein the enhancers are oriented in a natural orientation.

4. The construct of claim 1, wherein there are 3 or more enhancers.

5. The construct of claim 1, wherein there are from 2 to 5 enhancers.

6. The construct of claim 1, wherein the promoter comprises minimal promoter from the slow troponin I gene.

7. The construct of claim 1, further comprising an intron downstream of the promoter.

8. The construct of claim 1, wherein the enhancers are three enhancers each comprising the nucleotide sequence as set forth in nucleotides 57 to 218 of SEQ ID NO: 17.

9. The construct of claim 1, wherein the enhancers are three enhancers each comprising the nucleotide sequence as set forth in nucleotides 152 to 218 of SEQ ID NO: 17.

10. The construct of claim 1, wherein the enhancers are four enhancers each comprising the nucleotide sequence as set forth in nucleotides 57 to 218 of SEQ ID NO: 17.

11. The construct of claim 1, wherein the enhancers are four enhancers each comprising the nucleotide sequence as set forth in nucleotides 152 to 218 of SEQ ID NO: 17.

12. The construct of claim 1, wherein the enhancers are five enhancers each comprising the nucleotide sequence as set forth in nucleotides 57 to 218 of SEQ ID NO: 17.

13. The construct of claim 1, wherein the enhancers are five enhancers each comprising the nucleotide sequence as set forth in nucleotides 152 to 218 of SEQ ID NO: 17.

14. A method of specifically expressing a nucleotide sequence of interest in a muscle cell in vitro, comprising transfecting into the muscle cell a construct of claim 1; culturing said cell under suitable condition to express the nucleotide sequence of interest.

15. The method of claim 14, wherein the muscle cell is a skeletal muscle cell.

16. The method of claim 14, wherein the nucleotide sequence of interest codes for a protein.

17. The method of claim 16, wherein the protein mitigates pathology associated with hemophilia, Pompe disease, Fabry's disease, anaemia, emphysema or familial hypercholesterolemia.

18. The method of claim 16, wherein the protein mitigates pathology associated with a neuromuscular disorder.

19. A method of specifically expressing a nucleotide sequence of interest in a muscle cell in a mouse model, comprising administering the construct of claim 1 into a muscle cell of a mouse; measuring the expression of the nucleotide sequence of interest in said muscle cell.

* * * * *